United States Patent
Sun

(10) Patent No.: US 8,502,019 B2
(45) Date of Patent: Aug. 6, 2013

(54) METHODS FOR PRODUCING A HYBRID SEED PRODUCT

(75) Inventor: Paul Sun, Roscoe, IL (US)

(73) Assignee: Dairyland Seed Co., Inc., West Bend, WI (US)

( * ) Notice: Subject to any disclaimer, the term of this patent is extended or adjusted under 35 U.S.C. 154(b) by 710 days.

(21) Appl. No.: 12/409,010

(22) Filed: Mar. 23, 2009

(65) Prior Publication Data

US 2009/0249505 A1    Oct. 1, 2009

Related U.S. Application Data

(63) Continuation of application No. 11/146,365, filed on Jun. 6, 2005, now abandoned.

(51) Int. Cl.
*A01H 1/02* (2006.01)
*A01H 1/04* (2006.01)

(52) U.S. Cl.
USPC .......................................... 800/260; 800/266

(58) Field of Classification Search
None
See application file for complete search history.

(56) References Cited

U.S. PATENT DOCUMENTS

| | | |
|---|---|---|
| 3,570,181 A | 3/1971 | Davis |
| 3,842,538 A | 10/1974 | Barabas |
| 4,045,912 A | 9/1977 | Sun |
| 4,077,157 A | 3/1978 | Brander |
| 4,096,661 A | 6/1978 | Cleckner |
| 4,254,580 A | 3/1981 | Ferguson |
| 4,292,760 A | 10/1981 | Krave |
| 4,326,358 A | 4/1982 | Lawrence, Jr. et al. |
| RE31,023 E | 9/1982 | Hall, III |
| 4,351,130 A | 9/1982 | Rutger et al. |
| 4,545,146 A | 10/1985 | Davis |
| 4,648,204 A | 3/1987 | Davis |
| 4,684,612 A | 8/1987 | Hemphill et al. |
| 4,755,210 A | 7/1988 | Devlin |
| 4,822,949 A | 4/1989 | Niego et al. |
| 5,038,518 A | 8/1991 | Davis |
| 5,157,207 A | 10/1992 | Carlson et al. |
| 5,176,735 A | 1/1993 | Bell |
| 5,306,864 A | 4/1994 | Petolino |
| 5,324,646 A | 6/1994 | Buising et al. |
| 5,724,767 A | 3/1998 | Sun |
| 6,018,101 A | 1/2000 | Zhang et al. |
| 6,051,759 A | 4/2000 | Sun |
| 6,166,306 A | 12/2000 | Bowman |
| 6,320,098 B1 | 11/2001 | Sun et al. |
| 6,359,199 B1 | 3/2002 | Sun |
| 6,774,280 B2* | 8/2004 | Sun et al. ................... 800/260 |
| 2003/0172410 A1* | 9/2003 | Sun et al. ................... 800/298 |
| 2006/0277618 A1 | 12/2006 | Sun |

FOREIGN PATENT DOCUMENTS

| | | |
|---|---|---|
| WO | WO 96/19104 | 6/1996 |
| WO | WO 02/07504 | 1/2002 |
| WO | WO 02/060238 | 8/2002 |

OTHER PUBLICATIONS

Pedersen et al. Crop Sci. 13: 72-75, 1973.*
ASOCA Publication of Hybrid Alfalfa Certifloation, "Genetic and Crop Standards," (2001) 2-4 to 2-6.
Barnes, D.K. et al., "Fall dormancy score in alfalfa: a valuable predictive tool," Report of the 26th Alfalfa Improvement Conference, Brookings, S.D. (Jun. 6-8, 1978) p. 34.
Belanger, G. et al., "Effects of harvesting systems on yield, persistence and nutritive value of alfalfa," Canadian J. Plant Sci. (1992) 72(3) Database CABA AN92; 128874 Abstract.
Bula, R et al., "Population characterics of advanced generations of and alfalfa synthetic increased from selfed, single-cross, or polycross seed," Crop Science (1974) 14:618-621.
Elgin, J. et al., "Use of strain crosses in the development of multiple pest resistance alfalfa with improved field performance," Crop Science (1983) 23:57-64.
Elgin, Jr., "Breeding for disease and nematode resistance," Alfalfa and Alfalfa Improvement, edited by A.A. Hanson et al., No. 29 in the series Agronomy (1988) 827-858.
Fehr, W.R., Principles of Cultivar Development. Theory and Technique, MacMillan Publishing Company, Inc. (1987) 1(33):417-427.
Gjuric, R. et al., "Identification of cross-pollinated and self-pollinated progeny in alfalfa through rapd multiplex loci analysis," Crop Sci. (1996) 36(2):389-393.
Hill et al., "Effect of the number of parents on performance of alfalfa synthetics," Crop Sci. (1981) 21:298-300.
Pamphlet entitled "1995 Alfalfa Guide," AgriPro Seeds.
Pamphlet entitled "The Forage Package," Pioneer Brand Products for 1994-1995, pp. 16-17.
Pamphlet entitled, "Pioneer Brand Products for 1993-94," p. 14-16.
Pamphlet, W-L Research, Inc., 2000 Oak Street, Bakersfield, CA 93301.
Pedersen, M.W. et al., "Alfalfa seed size as an indicator of hybridity," Crop Science (1973) 13:72-75.
Poehlman, J.M., Breeding Field Crops, AVI Publishing Company, Inc. (1987) 652-655.
Pratt, R.G. et al., "Responses to selection for resistance to *Sclerotinia trifoliorum* in alfalfa bystem inoculations," Plant Dis. (1994) 78(8):826-829.

(Continued)

*Primary Examiner* — Shubo (Joe) Zhou
*Assistant Examiner* — Keith Robinson
(74) *Attorney, Agent, or Firm* — Michael Best & Friedrich LLP

(57) ABSTRACT

A method for increasing production of hybrid seed of bee-pollinated crops, such as alfalfa and soybean at predetermined hybridity levels. Hybrid seed is produced using female and pollenizer plants at a selected ratio of female plants to pollenizer plants. The female plants and the pollenizer plants are intermingled in the hybrid seed production field. Prediction of percentage of hybridity at various female to pollenizer ratios allows for selection of a ratio of female plants to pollenizer plants to provide seed at a test percentage of hybridity. The percentage of hybridity may be increased post-harvest by employing techniques using seed properties such as size differential, color or density to remove a higher percentage of non-hybrid seed. The hybrid seed product is maximized at various hybridity levels. Planting according to subrows allows for separate harvesting of intermingled crops. Testing the hybrid seed product provides verification of percentage of hybridity.

21 Claims, 4 Drawing Sheets

OTHER PUBLICATIONS

Song, S. et al., "General combining ability and its interaction with environments in a 7x7 diallel cross population of alfalfa," Crop Science (1974) 14:663-666.

European Office Examination Report for Application No. EP6760705.1 dated Jun. 11, 2008 (13 pages).

International Search Report and Written Opinion for Application No. PCt/US2006/021875 dated Oct. 24, 2006 (11 pages).

United States Patent Office Action for U.S. Appl. No. 08/326,183 dated Sep. 27, 1995 (8 pages).

United States Patent Office Action for U.S. Appl. No. 08/326,183 dated May 22, 1996 (10 pages).

United States Patent Office Action for U.S. Appl. No. 08/926,169 dated Oct. 2, 1998 (10 pages).

United States Patent Office Action for U.S. Appl. No. 08/926,169 dated Jun. 7, 1999 (5 pages).

United States Patent Office Action for U.S. Appl. No. 09/419,256 dated Dec. 20, 2000 (5 pages).

International Search Report for Application No. PCT/US1995/16645 dated Jun. 27, 1996 (3 pages).

Written Opinion for Application No. PCT/US1995/16645 dated Oct. 16, 1996 (4 pages).

United Slates Patent Office Action for U.S. Appl. No. 11/146,356 dated Oct. 31, 2007 (9 pages).

United States Patent Office Action for U.S. Appl. No. 11/146,356 dated Jul. 22, 2008 (10 pages).

Australian Patent Office Action or Application No. 2006255099 dated Oct. 5, 2010 (3 pages).

European Patent Office Action for Application No. 06760705.1 dated Oct. 7, 2010 (5 pages).

Australian Patent Office Action for Application No. 2006255099 dated Aug. 11, 2011 (3 pages).

* cited by examiner

METHODS FOR PRODUCING A HYBRID SEED PRODUCT

CROSS-REFERENCE TO RELATED APPLICATIONS

This application is a continuation of U.S. application Ser. No. 11/146,365, filed Jun. 6, 2005, which is incorporated herein by reference in its entirety.

BACKGROUND OF THE INVENTION

The present invention generally relates to methods for production of a hybrid seed product, and more particularly to methods for producing a hybrid seed product while increasing production of hybrid seed of bee-pollinated crops at predetermined hybridity levels, including post production adjustment of percentage of hybridity and verification of percentage of hybridity of the hybrid seed product after harvest.

Hybrid plant varieties offer many desirable agronomic traits. Hybrid plant varieties often provide higher yield than non-hybrid strains. Hybrid plant varieties may also possess higher stress tolerance than non-hybrid varieties, enabling them to survive in less favorable environmental conditions. Furthermore, hybrid plant varieties provide greater efficiency in breeding improvements. Hybridization allows for combination of desirable agronomic traits from different strains.

While hybridization provides these desirable agronomic traits, certain plant species present particular challenges to hybridization. Species such as corn are easily hybridized because the male and female reproductive organs have physical separation. Other species have reproductive parts that are less accessible and have little physical separation between male and female parts. These species are more difficult to hybridize. Bee-pollinated crops, such as alfalfa and soybeans, are examples of species that have male and female reproductive parts that have little physical separation because of the relatively small size of the flower.

Hybrid seed production in these species often employs cytoplasmic male sterile plants, also called female plants. Seed that is produced by female plants from pollinations by pollenizer plants, also called male plants, is mostly hybrid seed. Seed produced from selfing or sibbing by the pollenizer plants is mostly non-hybrid seed. During production of hybrid seed, employing a higher proportion of female plants to pollenizer plants in a hybrid seed production field increases the proportion of hybrid seed to non-hybrid seed. However, current methods for producing hybrid seed result in a significant decrease of seed yield for each individual plant when increasing the proportion of female plants to pollenizer plants. There is therefore a need for methods for increasing the proportion of hybrid seed to non-hybrid seed while maintaining high overall seed yield for a hybrid seed product.

Production of hybrid varieties is subject to federal law requirements that make a high percentage of hybridity very desirable. 7 CFR §201.26 requires that a variety have at least seventy-five percent hybridity to be classified as a hybrid variety. Certain plant species, particularly bee-pollinated species, such as alfalfa and soybeans, present challenges to breeding plant varieties that meet this federally mandated hybridity level. U.S. Pat. No. 3,570,181, herein incorporated by reference, discloses a method for producing hybrid alfalfa using cytoplasmic male sterile alfalfa plants. However, production according to this method results in large reduction of seed yield that makes production of hybrid seed of bee-pollinated crops commercially impractical. U.S. Pat. No. 4,045,912, herein incorporated by reference, discloses a method for producing seed but does not provide for production of seed meeting federal requirements for a hybrid variety. U.S. Pat. No. 4,045,912 is further not concerned with verification of percentage of hybridity at commercial levels of production. Thus, there is a need for methods for production of hybrid seed that provide for high seed yield while maintaining hybridity levels meeting federal requirements.

Production of a certified hybrid alfalfa product requires determination of percentage of hybridity. Determination of percentage of hybridity is often accomplished using methods employing morphological or molecular markers. However, using molecular markers is expensive, takes significant time and is often commercially impractical. In some species, morphological markers require a homozygous recessive gene on one side, and dominance gene on the other side, and are therefore difficult to employ. Furthermore, some plant species present additional difficulties to employing such methods. For example, tetraploid species such as alfalfa have greater complexity in their genetics and inheritance. Another difficulty is the small seed size of some species, such as alfalfa. There is therefore a need for methods for determining or verifying the percentage of hybridity of a particular hybrid that avoid these difficulties.

Separate harvesting of female seed and pollenizer seed is useful for determining percentage of hybridity. Prior methods of separate harvesting for species such as alfalfa require planting female seed and pollenizer seed in separate rows for separate harvesting. However, production of hybrid seed for bee-pollinated crops, such as alfalfa and soybeans, benefits from intermingling to allow a higher percentage of cross-pollination to occur. Planting in separate rows decreases production of hybrid seed, as cross-pollination becomes less frequent due to the distance of the female plants from the pollenizer plants. Where multiple female rows are planted for every male row, such as shown in U.S. Pat. No. 3,570,181, cross-pollination becomes even less frequent. There is therefore a need for methods for separately harvesting female seed and pollenizer seed that allow for intermingling of female and pollenizer plants.

Production of a hybrid seed product is furthermore a long, expensive and labor-intensive process. Prior methods of seed production do not provide for prediction of percentage of hybridity. A method for predicting hybridity levels of seed production of bee-pollinated crops would facilitate production of a hybrid seed product meeting federal standards. This would allow for faster, cost-effective and less labor-intensive production. There is therefore a need for methods for predicting hybridity levels of bee-pollinated crops.

Prior methods of seed production also do not include methods for post-production adjustment of hybridity levels of bee-pollinated crops. A method for adjusting hybridity levels of bee-pollinated crops would also aid meeting hybridity standards for production of hybrid plant varieties. Post-production adjustment of hybridity levels also would allow for production of hybrid plant varieties while employing breeding methods that would not normally result in hybridity levels required by statute. There is therefore a need for post-production methods for adjusting hybridity levels of bee-pollinated crops.

Although hybrid plant varieties are desirable for agronomic reasons, commercial production of many hybrid plant varieties has not been commercially viable, particularly for bee-pollinated crops. The present invention solves these needs and other problems in the field of hybrid seed production by providing, in most preferred aspects, methods for producing a hybrid seed product that includes increasing production of hybrid seed of bee-pollinated crops at predetermined hybridity levels, prediction of percentage of hybridity, determination of percentage of hybridity, post-production adjustment of percentage of hybridity, and verification of percentage of hybridity after harvest.

SUMMARY OF THE INVENTION

The invention therefore provides a method for producing a hybrid seed product of bee-pollinated crops, such as alfalfa and soybean, at predetermined hybridity levels. Hybrid seed is produced using female and pollenizer plants at a predetermined ratio of female plants to pollenizer plants mixed together in a hybrid seed production field. Prediction of percentage of hybridity at various female to pollenizer ratios allows for selection of a ratio of female plants to pollenizer plants to provide seed at a selected percentage of hybridity. The percentage of hybridity of the hybrid seed product may be increased after harvesting by employing techniques using seed properties such as size differential, color or density to remove a higher percentage of non-hybrid seed.

In other aspects of the present invention, the method provides for maximization of seed yield at various hybridity levels.

In further aspects of the present invention, the method provides for separate harvesting of intermingled crops.

In further aspects of the present invention, the method provides for verification of percentage of hybridity of a hybrid product.

These and further objects and advantages of the present invention will become clearer in light of the following detailed description of an illustrative embodiment of this invention.

BRIEF DESCRIPTION OF THE DRAWINGS

The illustrative embodiment may best be described by reference to the accompanying drawings where.

Figure 1:
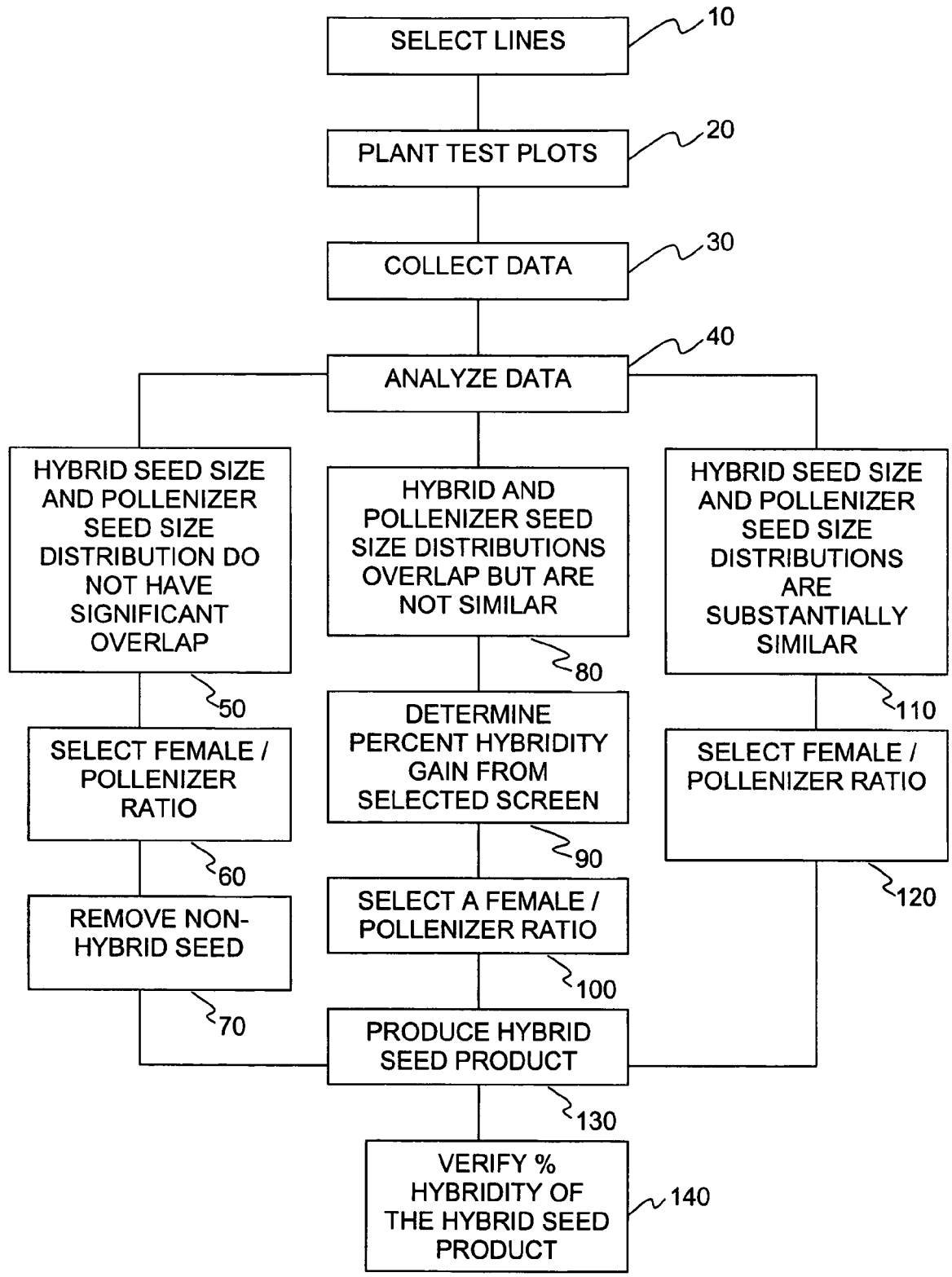
FIG. 1 shows a flow diagram of one embodiment of the methods for producing a hybrid seed product.

All figures are drawn for ease of explanation of the basic teachings of the present invention only; the extensions of the figures with respect to number, position, relationship, and dimensions of the parts to form the preferred embodiment will be explained or will be within the skill of the art after the following description has been read and understood. Further, the exact measurements and measurement proportions to conform to specific percentages, sizes, and similar requirements will likewise be within the skill of the art after the following description has been read and understood. Values provided are representative and are utilized to facilitate the description of the preferred embodiment.

Where used in the various figures of the drawings, the same numerals designate the same or similar parts. Furthermore, when the terms "upper," "lower," "side," "end," "bottom," "first," "second," "laterally," "longitudinally," "row," "column," "array," and similar terms are used herein, it should be understood that these terms have reference only to the structure shown in the drawings as it would appear to a person viewing the drawings and are utilized only to facilitate describing the illustrative embodiment.

DETAILED DESCRIPTION OF THE PREFERRED EMBODIMENT

The present invention provides methods for producing a hybrid seed product of bee-pollinated crops such as alfalfa and soybean. FIG. 1 shows a flow diagram of one example embodiment of these methods. The method includes selection of a female line and a pollenizer line 10. These lines are planted in test plots in selected ratios of female plants to pollenizer plants 20. Data is collected from the test plots 30. Data analysis provides information on characteristics such as: seed size distribution for each line and seed yield of female and pollenizer plants in response to the selected ratios of female plants to pollenizer plants 40. In the preferred embodiment, the data analysis can provide for further selection of a female line or lines and further selection of a pollenizer line or lines for production of the hybrid seed product. In one example embodiment, the data analysis 40 may indicate a combination of a female line and pollenizer line having a high seed yield.

In this example embodiment, analysis of seed size distribution determines a procedure for producing the hybrid seed product. If the seed size distribution of the female plants and the pollenizer plants have a small amount of overlap 50, then a female to pollenizer ratio is selected using the data analysis to produce the maximum quantity of seed 60. In one example embodiment, selection of a female to pollenizer ratio to produce the maximum quantity of seed occurs when the overlap in seed size distribution involves less than 25% of the seed product of the cross between the selected female line and the selected pollenizer line. Subsequent seed size screening removes enough non-hybrid seed to achieve a targeted percentage of hybridity in the hybrid seed product. Where there is little or no overlap in seed size distribution, substantially all of the non-hybrid seed may be removed 70.

If the seed size distribution of the female plants and seed size distribution of the pollenizer plants have significant overlap, but are not substantially the same 80, then statistical analysis on the respective seed size distributions determines the percentage of hybridity that can be gained by screening out seed within a selected size range 90. Selection of a female to pollenizer ratio for a production field takes into account both the hybridity level of the selected female to pollenizer ratios in the test plots, and the gain in hybridity level attained by screening out seed in a selected size range 100. In the preferred embodiment, the ratio producing the maximum quantity of seed after post-harvest screening to achieve a targeted hybridity level is selected for use in the production field.

If the seed size distribution of the female plants and the seed size distribution of the pollenizer plants are substantially the same 110, then a female to pollenizer ratio is selected for the production field using data from the test plots that will achieve the targeted hybridity level 120.

The selected female line and the selected pollenizer line are then planted in the production field in the selected female to pollenizer ratio to produce the hybrid seed product 130. After production, the percentage of hybridity of the hybrid seed product is verified 140.

With respect to the selection of lines 10 for the hybrid seed product, in the preferred embodiment of the methods of the invention, the production of a hybrid seed product includes selection of one or more female lines, also referred to as an "A line." A female line is a cytoplasmic male sterile line, a genic male sterile line, or an induced male sterile line by chemicals or biotechnology. These lines have a condition in which pollen is absent or non-functional in flowering plants. The methods also include the selection of one or more pollenizer lines, also referred to as a "male line" or "C line." The pollenizer line is a male fertile line having a condition in which pollen is produced and functional in flowering plants, with the female part either functional or not functional.

In the preferred embodiment, selection of the female line and the pollenizer line takes into account both agronomic factors and factors that affect percentage of hybridity and seed yield. In an example embodiment, these factors include: female to pollenizer ratio, seed yield from pollenizer plants, seed yield from female plants, female to pollenizer seed yield differential, female to pollenizer seed size differential, high seed yield with increasing female to pollenizer plant ratio, low P.P.I. (Pollen Production Index), large seed size, pollination power in pollenizer plants and high self-incompatibility in pollenizer plants. In further aspects of the invention, these factors include desirable agronomic traits such as disease resistance, insect resistance and forage yield.

The selected lines can then be planted in test plots 20 for data collection 30 and data analysis 40. In the preferred embodiment, data on seed yielding ability, pollination power, pollen production index (P.P.I.), seed size distribution for each line and seed yield of female and pollenizer plants in response to the selected ratios of female plants to pollenizer plants is collected along with other characteristics.

The data collection 30 and data analysis 40 of the present invention demonstrate that individual female lines can have different seed yielding abilities. Table 1 illustrates test results of seed yield for four female lines with different P.P.I., with each female line crossed with five different pollenizers.

TABLE 1

Seed Yield of Female Plants with Different P.P.I.

| Female Line (AXB) | P.P.I. | Average seed Yield (Total wt. of 4 rows in grams) |
|---|---|---|
| Female1 | 0.013 | 328.6 |
| Female2 | 0.025 | 402.1 |
| Female3 | 0.046 | 318.2 |
| Female4 | 0.085 | 369.6 |

Table 1 illustrates the results of testing under the following conditions:

Selection of four female lines with different P.P.I. and five pollenizer lines with different pollinating abilities for diallel mating in three female to pollenizer ratios, 70:30, 75:25, and 80:20 at two locations, Sloughouse, Calif., and Homedale, Id.

Split plot designs with two replications were used at the two locations. Each location included 120 plots, with each plot having six rows and being 20 feet long. The center four rows included a mixture of both female and pollenizer seed in one of the tested ratios. The outside rows included only female seed and provided for P.P.I. readings and progeny testing.

These four female lines demonstrate different seed yielding capabilities. As further shown in Table 1, experimentation reveals no significant correlation between P.P.I. and seed yields for the tested female lines in the tested female to pollenizer ratios within the tested low P.P.I. range. In this experiment, each female line was crossed with five male lines in three female to pollenizer ratios. Thus, in a preferred embodiment of the invention, the methods of the invention for hybrid seed production includes selection of at least one female line having a high seed yield, such as the line designated Female2 in the study above, without regard for the P.P.I. of the female line. In other aspects of the present invention, the invention may employ multiple female lines having varying seed yield. Those skilled in the art will recognize that selection of a female line may be done according to various agronomic factors within the spirit and scope of the invention.

In the preferred embodiment of the present invention, selection of a pollenizer, or male, line provides for high pollination power. Thus, a measure of pollination power provides a measure of average female line seed yield from pollination of the selected pollenizer line. Tables 2 and 3 show representative measures of pollination power for five male lines.

TABLE 2

Seed Yield of Pollenizers

| Pollenizer | Seed Yield (grams/plant) |
|---|---|
| Male1 | 361.5 |
| Male2 | 333.5 |
| Male3 | 360.8 |
| Male4 | 440.7 |
| Male5 | 276.6 |

Table 2 shows data collected according to the teachings of the present invention on average seed yield for five pollenizers crossed with four different females in three female to pollenizer ratios: 80:20, 75:25 and 70:30. Seed were harvested in bulk, comprising a mixture of both hybrid and pollenizer seed. Seed yields are the mean of twenty-four plots. The Male5 pollenizer line had the white flower trait.

Testing according to the teachings of the present invention indicates that different pollenizers have different seed yielding abilities and varying pollinating power with respect to female plant seed yield. In the study performed above, the Male4 pollenizer caused the female plants to produce the most seed, and the Male5 pollenizer caused the female plants to produce the least seed. These results are statistically significant at the 1% level.

TABLE 3

Average Seed Yield of Each Female with Specific Pollenizer (Male) at Three Female to Male Ratios (70:30, 75:25, and 80:20)

| Female | Male | | | | |
|---|---|---|---|---|---|
| | Male1 | Male2 | Male3 | Male4 (High seed) | Male5 (Low seed) |
| Female1 | 316.8 | 339.2 | 316.8 | 383.8 | 286.7 |
| Female2 (high seed yielder) | 431.2 | 392.5 | 361.5 | 534.3 | 290.8 |
| Female3 (low seed yielder) | 297.0 | 298.5 | 358.0 | 402.3 | 235.3 |
| Female4 | 401.2 | 303.7 | 406.8 | 442.8 | 293.5 |

Testing according to the teachings of the present invention confirm that crossing females having high seed yield with pollenizers having high seed yield results in a cross with the highest seed yield. Likewise, crossing females having low seed yield with pollenizers having low seed yield results in a cross with the lowest seed yield. Table 3 summarizes the results of this testing.

According to the further teachings of the present invention, the percentage of hybridity of the hybrid seed product will be highest when using a male line with high pollination power but low seed yield. This provides for a higher percentage in the production field of hybrid seed by lowering production of non-hybrid seed. In the preferred form of the invention, the method includes selection of a male line with low seed yield but high pollination power for crossing with a female line with high seed yield in hybrid seed production. In another aspect of the preferred embodiment of the invention, pollenizers having high self-incompatibility contribute to a hybrid seed product having less selfed seed than outcross seed. As with selection of the female line, in other aspects of the present invention, the method of the invention may employ multiple pollenizer lines having varying pollination power. Those skilled in the art will recognize that selection of a pollenizer line having lower pollination power and lower self-incompatibility is within the spirit and scope of the invention, and that selection of a pollenizer line may be done according to various agronomic factors.

TABLE 4

Seed Yield Decrease with Increase Female and Decrease Pollenizer (Male) in Female to Male Ratios

| | Female:Pollenizer (male) | | |
|---|---|---|---|
| | 70:30 | 75:25 | 80:20 |
| Seed Yield (Hybrid seed and pollenizer seed) | 375.2 | 370.1 | 318.6 |
| % reduction from 70:30 seed production level | | 1.4 | 15.1 |

In the most preferred embodiment of the invention, the method for production of hybrid seed further incorporates selection of female to pollenizer ratios. Testing according to the teachings of the present invention demonstrates that female to pollenizer ratio affects seed yield, as shown in Table 4. This testing further indicates that the effect of female to pollenizer ratio is not linear. In one example embodiment, experimentation on selected female and pollenizer lines demonstrates an average 1.4% drop in seed yield between a 70:30 and a 75:25 female to pollenizer ratio. However, testing demonstrated an average 15.1% drop in seed yield between a 75:25 and an 80:20 female to pollenizer ratio. Therefore, for the tested lines, much greater gains in seed yield occur when going from an 80:20 female to pollenizer ratio to a 75:25 ratio than from a 75:25 ratio to a 70:30 ratio. Table 4 summarizes the average decreases in seed yield with increasing female to pollenizer ratios for the tested varieties. Furthermore, testing according to the teachings of the present invention further demonstrates that the decrease in seed yield will vary with different female to pollenizer crosses, as shown in Tables 6, 7, 8, and 9.

According to the teachings of the present invention, individual crosses have varying responses to female to pollenizer ratio with respect to hybrid seed production levels and percentages of hybridity. Thus, in the preferred form of the invention, production of a hybrid seed product includes determining, for each cross, the hybrid seed production level and percentage of hybridity for a range of female to pollenizer ratios. In this preferred embodiment, hybrid seed production employs selection of a specific female to pollenizer ratio for maximum seed production at a desired hybridity level for each cross of two or more lines. However, those skilled in the art will recognize that selection of a female to pollenizer ratio can be made for a selected cross without determining the hybrid seed production level and percentage of hybridity for a range of female to pollenizer ratios. For example, in one alternate embodiment, a typical response to female to pollenizer ratio may be used for production purposes without determining individual response to female to pollenizer ratio. In another alternate embodiment, where non-hybrid seed are removed to produce the hybrid seed product, a female to pollenizer ratio having high hybrid seed production levels, such as 70:30 or 60:40 is selected for production.

TABLE 5

Seed Yield of a Female Line Pollinated with High and Low Seed Yield Pollenizers at Three Different Female to Pollenizer Ratio's

| | Female:Male ratio | | | | C1/C2 | A1 × C1/A1 × C2 |
|---|---|---|---|---|---|---|
| | 1:1 | 2:1 | 3:1 | total | ratio | ratio |
| F(A) (wt/plant in grams) | 59.9 | 48.6 | 38.9 | 147.4 | | |
| M C1 (High yield) (wt/plant in grams) | 45.2 | 37.4 | 39.5 | 122.1 | 122.1/35.3 | 147.4/46.1 |
| % Hybridity | (56.9) | (72.2) | (74.8) | | | |
| F (A) (wt/pl) in grams | 17.4 | 15.3 | 13.4 | 46.1 | | |
| M C2 (Low yield) (wt/plant in grams) | 12.9 | 11.8 | 10.6 | 35.3 | | |
| Avg. Female seed wt. | 38.7 | 32.0 | 26.2 | | | |
| Ave. Male seed wt. | 29.1 | 24.6 | 25.1 | | | |
| % Hybridity | (62.5) | (73.1) | (79.9) | | | |

In one preferred embodiment of the method of the invention to produce a hybrid seed product, selection of a cross having a high female to pollenizer seed yield differential provides for an increase in the percentage of hybridity of the hybrid seed product. The teachings of the present invention demonstrates that seed yield of female plants varies in response to different males at different female to pollenizer ratios. Table 5 illustrates results of seed yield for a female line crossed with a high seed yield pollenizer and a low seed yield pollenizer at three different female to pollenizer ratios. Thus, greater levels of hybridity can be obtained by selection for a cross where the pollenizer lines and female lines have a high female to pollenizer seed yield differential. In the preferred embodiment, the methods for producing a hybrid seed product of the instant invention include selection of a female line and a pollenizer line to provide for a high female to pollenizer seed yield differential.

The present invention further illustrates, as shown in Table 5, that female seed yield has a positive correlation with decreasing female to pollenizer ratios. Total seed yield also has a positive correlation with decreasing female to pollenizer ratios. In contrast, the percentage of hybridity has a positive correlation with increasing female to pollenizer ratios. Female seed yield is also affected by pollenizer seed yield, with higher pollenizer seed yield positively correlated to higher female seed yield.

TABLE 6

Female1 with Male1
Seed Yield Decrease and Hybridity Increase as Female to Male
(Pollenizer) Ratios Changed from 1:1 Ratio to 2:1 Ratio and 3:1 Ratio

|  | Female:Male | | |
|---|---|---|---|
|  | 1:1 | 2:1 | 3:1 |
| F1 (wt/pl) grams | 59.9 | 48.6 | 38.9 |
| % reduction from 1:1 seed production level |  | 18.9 | 35.1 |
| M1 (wt/pl) grams | 45.2 | 37.4 | 39.5 |
| % reduction from 1:1 seed production level |  | 17.3 | 12.6 |
| Total (Female + Male) | 105.1 | 86.0 | 78.4 |
| % reduction from 1:1 seed production level |  | 18.2 | 25.4 |
| F:M seed yield differential | 1.33 | 1.30 | 0.98 |
| % Hybridity | 57.0 | 72.2 | 74.7 |

TABLE 7

Female1 with Male2
Seed Yield Decrease and Hybridity Increase as Female to Male
(Pollenizer) Ratios Changed from 1:1 Ratio to 2:1 Ratio and 3:1 Ratio

|  | Female:Male | | |
|---|---|---|---|
|  | 1:1 | 2:1 | 3:1 |
| F1 (wt/pl) grams | 17.4 | 15.3 | 13.4 |
| % reduction from 1:1 seed production level |  | 12.1 | 23.0 |
| M2 (wt/pl) grams | 12.9 | 11.8 | 10.6 |
| % reduction from 1:1 seed production level |  | 8.5 | 17.8 |
| Total (Female + Male) | 30.3 | 27.1 | 24.0 |
| % reduction from 1:1 seed production level |  | 10.6 | 20.8 |
| F:M seed yield differential | 1.35 | 1.30 | 1.26 |
| % Hybridity | 62.5 | 73.1 | 79.9 |

TABLE 8

Overall changes in
Seed Yield Decrease and Hybridity Increase as Female to Male
(Pollenizer) Ratios Increases from 1:1 Ratio to 2:1 Ratio and 3:1 Ratio

|  | Female:Male | | |
|---|---|---|---|
|  | 1:1 | 2:1 | 3:1 |
| F1 (wt/pl) grams | 59.9 | 48.6 | 38.9 |
| Change | 100.0 | 81.1 | 64.9 |
| M1 (wt/pl) grams | 45.2 | 37.4 | 39.5 |
| Change | 100.0 | 82.7 | 87.4 |

TABLE 8-continued

Overall changes in
Seed Yield Decrease and Hybridity Increase as Female to Male
(Pollenizer) Ratios Increases from 1:1 Ratio to 2:1 Ratio and 3:1 Ratio

|  | Female:Male | | |
|---|---|---|---|
|  | 1:1 | 2:1 | 3:1 |
| Total (Female + Male) | 105.1 | 86.0 | 78.4 |
| Change | 100.0 | 81.8 | 74.6 |
| F:M seed yield differential | 1.33 | 1.30 | .99 |
| % Hybridity | 56.9 | 72.2 | 74.8 |

Tables 6, 7 and 8 show data for a female line crossed with two pollenizer lines using three different female to pollenizer ratios. Table 6 shows the female line crossed with a first pollenizer line (Male1) at three female to pollenizer ratios. Table 7 shows the same female line crossed with a second pollenizer line (Male2) at three female to pollenizer ratios. Data obtained from experimentation according to the teaching of the present invention demonstrates an average hybridity level of 71.8% for the cross with the first pollenizer line and an average hybridity level of 67.8% for the cross with the second pollenizer line. Thus, according to the teachings of the present invention, percentage of hybridity will vary from cross to cross.

Figure 2A:
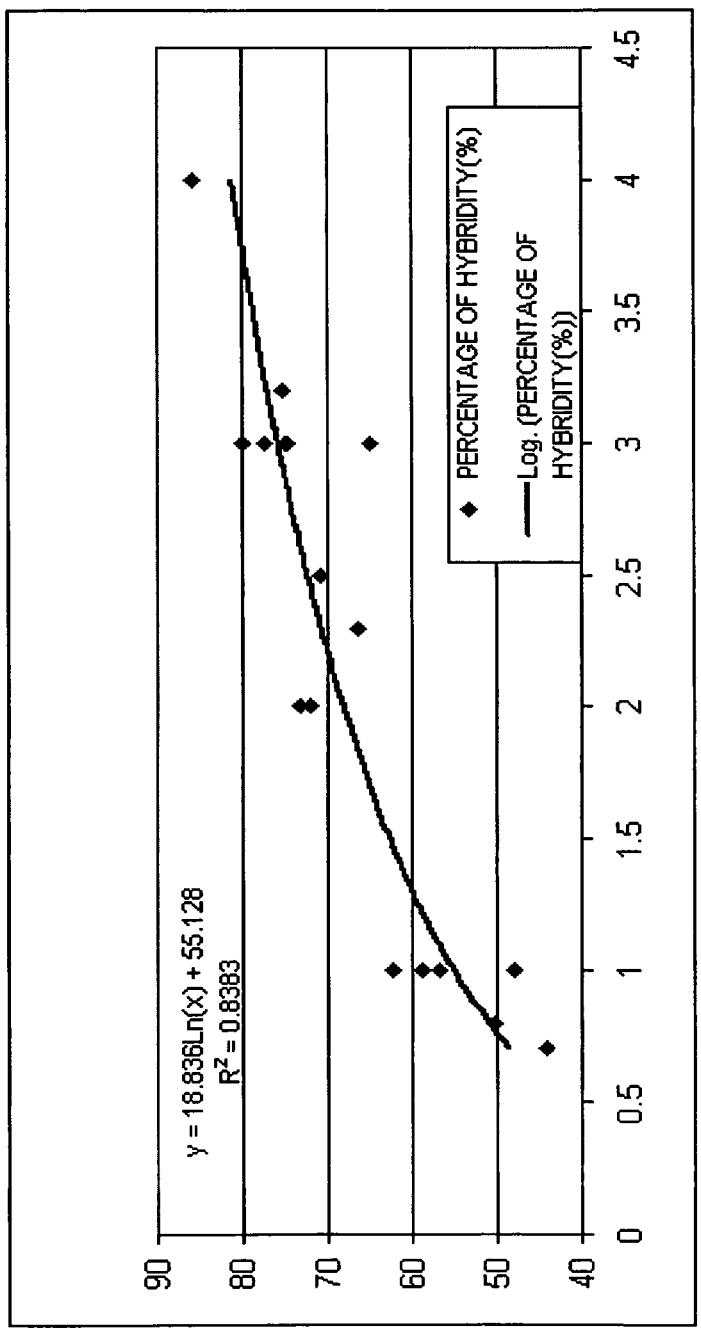
FIG. 2a shows a regression curve showing percentage hybridity versus female to pollenizer ratio for a single cross.

This experimentation further shows differences in response to seed yield and percentage of hybridity from cross to cross. Table 6 shows that for the first pollenizer (Male1), seed yield increased by 34% and 10% when female to pollenizer ratio changed from 3:1 to 1:1 and 3:1 to 2:1, respectively. Percentage of hybridity, conversely, increased by 31% and 27% when female to pollenizer ratios changed from 1:1 to 3:1 and 1:1 to 2:1, respectively. Table 7 shows that for the second pollenizer (Male2), seed yield increased by 26% and 13% when female to pollenizer ratio changed from 3:1 to 1:1 and 3:1 to 2:1, respectively. The percentage of hybridity increased by 28% and 17%, conversely, when female to pollenizer ratios changed from 1:1 to 3:1 and 1:1 to 2:1, respectively. Thus, according to the teachings of the present invention, in the preferred embodiment of the invention for producing a hybrid seed product, each cross is tested for responsiveness to female to pollenizer ratio for seed yield and percentage of hybridity. In the preferred embodiment, a cross is selected that maintains at least two-thirds of female seed yield when increasing ratio of female plants to pollenizer plants from 1:1 to 3:1 under substantially similar environmental conditions. Alternatively, for some varieties, the method for producing a hybrid seed product can make use of a generic formula to estimate responsiveness to female to pollenizer ratio for seed yield and percentage of hybridity. One way of establishing a generic curve is by estimating a curve from multiple crosses of other varieties. FIG. 2A shows one example embodiment of a curve estimated from several female-pollenizer crosses.

TABLE 9

The effect on hybrid seed yield and percentage of hybridity by changing female to pollenizer ratios.

| Female | | Female to Pollenizer Ratios. | | |
|---|---|---|---|---|
| | | 70:30 | 75:25 | 80:20 |
| F1 | SEED YIELD | 345 | 298 | 218 |
| | % CHANGE | 100 | 86 | 63 |
| | HYBRIDITY | 87.5 | 93.5 | 90.5 |
| | % CHANGE | 100 | 107 | 103 |
| F2 | SEED YIELD | 285 | 357 | 231 |
| | % CHANGE | 100 | 125 | 81 |
| | HYBRIDITY | 88.5 | 84.5 | 87.5 |
| | % CHANGE | 100 | 96 | 99 |
| F3 | SEED YIELD | 340 | 174 | 193 |
| | % CHANGE | 100 | 51 | 57 |
| | HYBRIDITY | 84.5 | 88 | 91 |
| | % CHANGE | 100 | 104 | 108 |
| F4 | SEED YIELD | 344 | 285 | 252 |
| | % CHANGE | 100 | 83 | 73 |
| | HYBRIDITY | 83.5 | 88.00 | 89.00 |
| | % CHANGE | 100 | 105 | 107 |
| OVER ALL CHANGE | SEED YIELD | 100 | 86 | 69 |
| | HYBRIDITY | 100 | 103 | 104 |

Figure 2B:
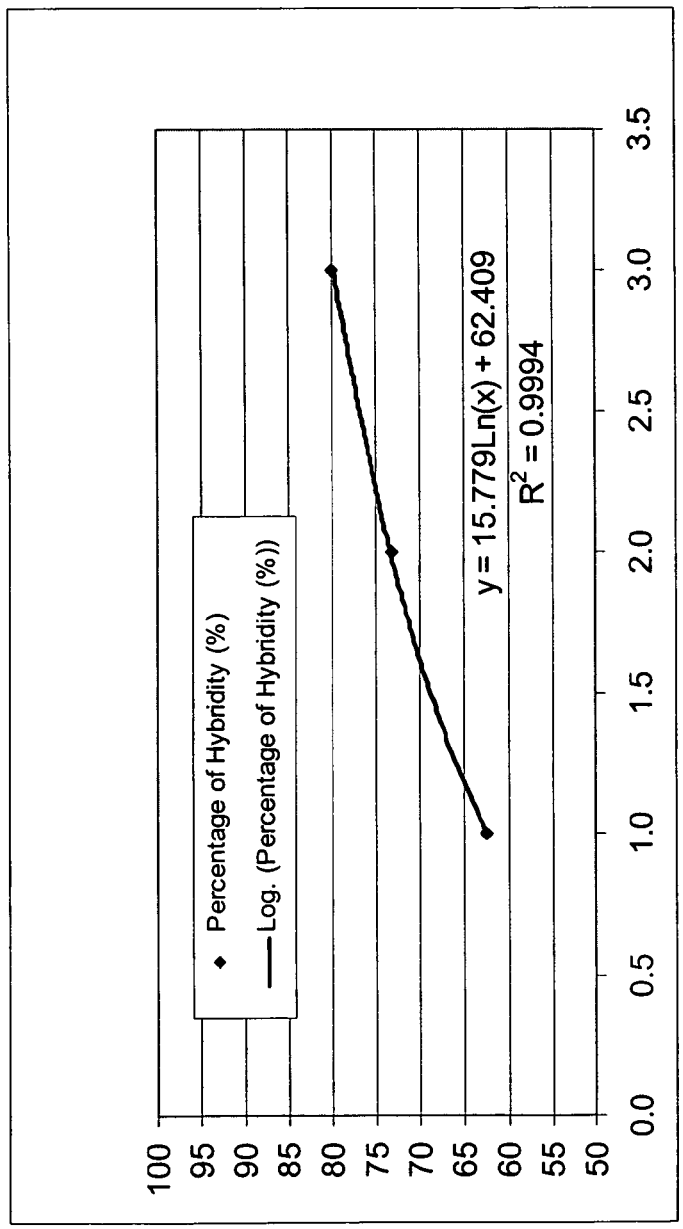
FIG. 2b shows a regression curve showing percentage hybridity versus female to pollenizer ratio for multiple crosses.

Table 9 summarizes further experimental seed yield and percentage of hybridity for multiple female and pollenizer crosses at different female to pollenizer ratios. In the most preferred embodiment, production of a hybrid seed product includes a statistical analysis on data for a selected cross in order to determine the effect of different female to pollenizer ratios on seed yield. In one example embodiment, the statistical analysis comprises a regression analysis. FIG. 2B shows a number of regression curves for different female-pollenizer crosses.

As shown in Table 9, according to the teachings of the present invention, changing female to pollenizer ratios from a 70:30 ratio to a 75:25 ratio or a 70:30 ratio to an 80:20 ratio greatly impacts hybrid seed yield. Seed yield dropped an average of 31% from a 70:30 ratio to 80:20 ratio and dropped an average of 16% from a 70:30 ratio to a 75:25 ratio, respectively, when Male3 was crossed with four different female lines. Average percentage of hybridity increased 3% when female to pollenizer ratios changed from a 70:30 ratio to a 75:25 ratio and increased 4% when going from a 70:30 ratio to an 80:20 ratio, respectively.

While a hybrid seed product having a high percentage of hybridity is desirable for agronomic qualities and for certification; on the other hand, the cost of producing a hybrid seed product increases with decreasing seed yield. The methods for producing a hybrid seed product of the present invention, therefore, provides methods for determining a female to pollenizer ratio providing for maximum seed yield at a predetermined level of hybridity of the hybrid seed product.

TABLE 10

Hybrid Seed Yield and Percentage of Hybridity are Different with Each Specific Combination of Female Line and Pollenizer at Different Female to Pollenizer Ratios

| | F:M | Female seed % of Male. | % Hybridity | Female seed yield Change % |
|---|---|---|---|---|
| F1:M1 | 0.7:1.0 | 78.7/100.0 | 44.0 | |
| | 3:1 | 61.6/100 | 64.9 | |
| Female ratio change. | | (0.7:1.00 to 3:1) | | (78.3%) |
| F2:M2 | 1.1:1.0 | 92.3/100.0 | 48.0 | |
| | 3.2:1.0 | 65.1/100 | 75.3 | |
| Female ratio change. | | (1.1:1.0 to 3.2:1.0) | | (70.5) |
| F3:M3 | 1:1 | 141.0 | 58.5 | |
| | 2.5:1 | 97.8/100 | 71.0 | |
| Female ratio change. | | (1:1 to 2.5:1) | | (69.4) |
| F1:M4 | 0.8:1.0 | 101.4/100 | 50.3 | |
| | 3.0:1.0 | 115.1/100 | 77.5 | |
| Female ratio change | | (0.8:1.0 to 3:1) | | (113.5) |
| 5 | 2.3:1.0 | 86.8/100 | 66.6 | |
| | 3.0:1.0 | 100/100 | 75.0 | |
| Female ratio change | | (2.3:1.0 to 3:1) | | (115.2) |

Table 10 summarizes experimentation according to the teachings of the present invention to determine varying effects of female to pollenizer ratios on different crosses. In this example embodiment, Female1 (F1), Female2 (F2) and Female3 (F3) seed yield decreased at higher female to pollenizer ratios when pollinated by Pollenizer1 (M1) and Pollenizer2 (M2). Female4 (F4) and Female5 (F5), on the other hand, did not show seed yield decrease at higher female to male ratios when pollinated by Pollenizer4 (M4) and Pollenizer5 (M5). With respect to the lines tested and reported on Table 9, (A1XB1)×(A2XR (Restorer)) cross demonstrates both higher hybrid seed yield and higher percentage of hybridity.

In the preferred embodiment of the invention, the data analysis 40 comprises a regression analysis of percentage of hybridity versus female to pollenizer ratio to establish a regression curve for each individual cross. In this embodiment of the present invention, selection of lines for hybrid seed production employs the resulting regression curves for each cross under consideration in order to select a cross for high seed yield during hybrid seed production. FIG. 2B shows a regression curve showing percentage hybridity versus female to pollenizer ratio for multiple crosses. In this example embodiment, the regression analysis shows:

$$y = 18.836 \ln(x) + 55.128$$

where:
y=percentage of hybridity
x=female to pollenizer ratio.

In this embodiment of the invention to produce a hybrid seed product, the regression analysis allows for determination of a female to pollenizer ratio necessary to achieve a targeted percentage of hybridity. In one example embodiment, selection of the female to pollenizer ratio employs the regression analysis to target a 75% hybridity level to achieve certification standards for a hybrid variety. In an alternative embodiment, selection of the female to pollenizer ratio employs the regression analysis to target a 95% hybridity level.

However, in many female to pollenizer crosses, seed yield dramatically decreases with increasing female to pollenizer ratios. Agronomic or other considerations often suggest a cross having a dramatic decrease in seed yield with increasing female to pollenizer ratios. Therefore, the present invention provides a means for post-production increase of percentage of hybridity in a hybrid seed product.

In the preferred embodiment of the invention, the method for production of a hybrid seed product increases the percentage of hybridity of a hybrid seed product by removing non-hybrid seed. In one example embodiment, removal of non-hybrid seed makes use of seed size differential between hybrid seed produced by female plants and non-hybrid seed produced by pollenizer plants. In this preferred embodiment, selection of a female line and selection of a pollenizer line results in hybrid seed having an average size larger than non-hybrid seed. In an alternate embodiment, selection of a female line and selection of a pollenizer line results in hybrid seed having an average size smaller than non-hybrid seed.

Testing according to the preferred teachings of the invention demonstrates selection of a female line and a pollenizer line can provide a cross having a high correlation (r=0.9) between female parental lines and their first generation progeny with respect to seed size. Thus, in the preferred embodiment, the methods for producing a hybrid seed product employs selection for hybrid seed having a seed size distribution skewed to larger seed sizes and non-hybrid seed having a seed size distribution skewed to smaller seed sizes. Sifting production seed to screen out seed smaller than a selected seed size increases the percentage of hybrid seed for the hybrid seed product. In one example embodiment, a sieve screens out seed smaller than a selected seed size to increase the percentage of hybridity of the hybrid seed product. In one example embodiment, shown in Table 14, using a $1/19$" sieve provides a gain to 75% hybridity when production of hybrid seed is done using a 65:35 ratio of female plants to pollenizer plants. As those skilled in the art will recognize, different sieve sizes can be employed to accomplish different increases in percentage of hybridity.

TABLE 13

Seed Size Distribution of a Female Line, 3 Pollenizers a Hybrid Using a $1/19$" sieve to $1/23$" sieve

| Entry | $1/19$ | $1/20$ | $1/21$ | $1/22$ | $1/23$ |
|---|---|---|---|---|---|
| Hybrid (A1 × B1) × C1, C2, C3 | 12.59% | 4.12% | 3.77% | 0.23% | 0.01% |
| Female (A × B) | 11.92% | 4.58% | 4.36% | 0.63% | 0.35% |
| Pollenizer (C1) | 47.37% | 26.93% | 24.87% | 2.87% | 0.23% |
| Pollenizer (C2) | 46.26% | 23.38% | 21.47% | 1.96% | 0.12% |
| Pollenizer (C3) | 18.54% | 8.90% | 8.32% | 1.11% | 0.27% |
| Pollenizer Average | 37.39% | 19.74% | 18.22% | 1.98% | 0.21% |

As shown in Table 12, seed size differential varies for each crossing of different female lines and pollenizer lines. Table 12 shows a seed size distribution for a hybrid line, a female line, and three pollenizer lines. Table 13 shows the percentage of seed screened out using five different sieve sizes, from $1/19$ to $1/23$.

According to the teachings of the present invention, seed size distributions vary for each different cross; therefore, increases in hybridity level also vary with each different cross between different female lines and different pollenizer lines. Because seed size is a inheritable trait, in the preferred embodiment of the present invention for producing a hybrid seed product, selection of female and pollenizer lines provides for seed size differential between hybrid and non-hybrid seed. Environmental conditions, such as drought and poor soil conditions, also affect seed size. Thus, determination of seed size distribution according to the teachings of the present invention, should be done in the same field to control for environmental variation. As the seed size distribution differential between female line and pollenizer line increases, the environmental effect on the use of screening to remove non-hybrid seed will be reduced. Experimentation according to the teaching of the present invention, and as shown in Table 14, illustrates the increase in hybridity levels achieved by straining out a selected seed size for crosses between one female line and three pollenizer lines. In particular, Tables 14a and 14b illustrate gains in hybridity level for a $1/19$" sieve and a $1/21$" size sieve for the selected crosses.

TABLE 12

Seed Size Distributions of a Female Line, 3 Pollenizers and a Hybrid

| (A1 × B1) × (C1 + C2 + C3) | $1/14$ | $1/15$ | $1/16$ | $1/17$ | $1/18$ | $1/19$ | $1/20$ | $1/21$ | $1/22$ | $1/23$ | REMAIN | MEAN |
|---|---|---|---|---|---|---|---|---|---|---|---|---|
| H1 (hybrid) | 0.49 | 14.99 | 25.22 | 25.72 | 20.97 | 8.47 | 0.35 | 3.54 | 0.22 | 0.01 | 0.00 | 5.93 |
| F1 (Female 1) | 1.17 | 18.60 | 23.73 | 26.24 | 18.11 | 7.54 | 0.22 | 3.72 | 0.28 | 0.35 | 0.00 | 5.96 |
| C1 (Pollenizer 1) | 0.73 | 1.46 | 4.47 | 15.56 | 29.18 | 21.97 | 2.09 | 21.49 | 2.58 | 0.19 | 0.29 | 5.37 |
| C2 (Pollenizer 2) | 0.56 | 2.08 | 7.21 | 21.01 | 21.86 | 24.32 | 1.91 | 19.14 | 1.80 | 0.12 | 0.00 | 5.45 |
| C3 (Pollenizer 3) | 0.80 | 10.64 | 21.78 | 27.68 | 20.08 | 10.16 | 0.58 | 7.17 | 0.83 | 0.26 | 0.01 | 5.82 |
| Mean of C1 + C2 + C3 | 0.70 | 4.73 | 11.16 | 21.41 | 23.71 | 18.82 | 1.53 | 15.93 | 1.74 | 0.19 | 0.10 | |

| | | 1,000 SEED WEIGHT |
|---|---|---|
| H1 | =(A1 × B1) × (C1, C2, C3) | 2.480 GRAMS |
| F1 | =A1 × B1 | 2.365 GRAMS |
| C1 | | 2.200 GRAMS |
| C2 | | 2.339 GRAMS |
| C3 | | 2.250 GRAMS |

TABLE 14a

Percentage of Hybridity Gained by Applying 1/19" Sieve and 1/21" Sieve to Screen Out a Higher Percentage of Non-Hybrid Seed (Pollenizer $C_1$, $C_2$, $C_3$)

| PARENTS | | AMT. SEED SCREEN OUT FOR 1/19 SIZE | | FEMALE:POLLENIZER | % HYBRIDITY | *% HYBRID FOR |
|---|---|---|---|---|---|---|
| FEMALE | POLLENIZER | FEMALE | POLLENIZER | RATIO | INC. | PRODUCT |
| A1 × B1 | C1 | 11.92% | 47.37% | 65:35 | 10.7 | 75.7 |
|  | C2 |  | 46.26% |  | 10.3 | 75.3 |
|  | C3 |  | 18.54% |  | 1.8 | 66.8 |
|  | C1 |  |  | 70:30 | 9.6 | 79.6 |
|  | C2 |  |  |  | 9.3 | 79.3 |
|  | C3 |  |  |  | 1.6 | 71.6 |
|  | C1 |  |  | 75:25 | 8.4 | 83.4 |
|  | C2 |  |  |  | 8.1 | 83.1 |
|  | C3 |  |  |  | 1.4 | 76.4 |
|  | C1 |  |  | 80:20 | 7.0 | 87.0 |
|  | C2 |  |  |  | 6.8 | 86.8 |
|  | C3 |  |  |  | 1.2 | 81.2 |

TABLE 14b

| PARENTS | | AMT. SEED SCREEN OUT FOR 1/21 SIZE | | FEMALE:POLLENIZER | % HYBRIDITY | % HYBRID FOR |
|---|---|---|---|---|---|---|
| FEMALE | POLLENIZER | FEMALE | POLLENIZER | RATIO | INC. | PRODUCT |
| A1 × B1 | C1 | 4.36% | 24.87% | 65:35 | 5.3 | 70.3 |
|  | C2 |  | 21.47% |  | 4.3 | 69.3 |
|  | C3 |  | 8.32% |  | 1.0 | 66.0 |
|  | C1 |  |  | 70:30 | 4.8 | 74.8 |
|  | C2 |  |  |  | 4.0 | 74.0 |
|  | C3 |  |  |  | 0.9 | 70.9 |
|  | C1 |  |  | 75:25 | 4.3 | 79.3 |
|  | C2 |  |  |  | 3.5 | 78.5 |
|  | C3 |  |  |  | 0.8 | 75.8 |
|  | C1 |  |  | 80:20 | 3.6 | 83.6 |
|  | C2 |  |  |  | 3.0 | 83.0 |
|  | C3 |  |  |  | 0.7 | 80.7 |

In alternate embodiments of the invention, the method for post-production increase of percentage of hybridity can employ differences in seed density, seed weight or seed coat color. In one example embodiment, selection of a female line and a pollenizer line may provide for non-hybrid seed having a lesser density than hybrid seed. In this example embodiment, the teachings of the present invention provides for removal of non-hybrid seed according to seed density or seed weight. A gravity table or rice roller can separate hybrid and non-hybrid seed in this embodiment of the invention. In an alternate embodiment employing differences in seed color between hybrid seed and non-hybrid seed, a seed coat color sorter removes non-hybrid seed. Those skilled in the art will recognize that other methods of removing non-hybrid seed to increase the percentage of hybridity of a hybrid seed product lie within the spirit and scope of the invention. For example, morphological traits such as seed size, seed color, seed weight, leaf shape, leaf size, root color, stem color, flower color root structure, plant height and fall growth habit or a genetic marker can be used to distinguish hybrid seed from non-hybrid seed.

Therefore, in the preferred embodiment of the invention to produce certified seed, the regression curve of a targeted hybrid product provides for selection of a female to pollenizer ratio, that when combined with a post-production increase in hybridity level, achieves maximum yield at a hybridity level of at least 75%.

In the preferred embodiment of the invention to produce a hybrid seed product, test plots provide for determination of percentage of hybridity at different female to pollenizer ratios. Regression analysis of percentage of hybridity versus female to pollenizer ratio then provides a regression curve for each individual cross to allow for production of a hybrid product having a preselected percentage of hybridity. In other aspects of the method of the invention, the test plots further provide for determination of the seed size distribution of selected female lines, male lines and hybrid lines. The test plots also provide for determination of the 1,000 seed weight of each line and the P.P.I. of the female lines.

In one example embodiment of the invention to produce a hybrid seed product, the following types of test plots are employed.

A "Check" plot has female seed and pollenizer seed planted in the same plot. The check plot includes two pollenizer rows, a skipped row, four female rows, a skipped row, and two pollenizer rows. This design of the "Check" plot allows the female rows and pollenizer rows to be harvested separately. After flowering, analysis of the female plants provides for determination of the P.P.I. After harvesting, analysis of the seed from the female plants provides determination of seed size distribution and 1000 seed weight. After harvesting the pollenizer plants, analysis of the seed from pollenizer plants provides determination of seed size distribution and 1000 seed weight. Analysis also determines data for the seed yield of female plants and pollenizer plants.

A female to pollenizer plot designed to have a 1:1 ratio. The female and pollenizer plants are intermingled and distributed randomly.

A female to pollenizer plot designed to have a 2:1 ratio. The female and pollenizer plants are intermingled and distributed randomly.

A female to pollenizer plot designed to have a 3:1 ratio. The female and pollenizer plants are intermingled and distributed randomly.

A female to pollenizer plot designed to have a 4:1 ratio. The female and pollenizer plants are intermingled and distributed randomly.

In one preferred embodiment, the test plots are planted using a complete random block design with four to eight replications for each female to pollenizer ratio. In this embodiment, the test plots are six row plots, with each row fifty to one hundred feet long. Data collection is performed on the middle two to four rows, with the outside rows serving as borders. The outside border rows serve as a guard and a barrier to reduce contamination from neighboring plots.

In this example embodiment of the invention, data collection follows the following procedures. The number of seed produced by female plants can be determined using the equation:

$$x = \text{female seed weight/weight of one thousand female seed},$$

where x=the mean number of seed produced by a female plant.

The number of seed produced by pollenizer plants can be determined using the equation:

$$y = \text{pollenizer seed weight/weight of one thousand pollenizer seed},$$

where y=the mean number of seed produced by a pollenizer plant.

The percentage of female seed can be then determined as:

$$\% \text{ female seed} = x/(x+y).$$

In the preferred embodiment of the invention, determination of percentage of hybridity takes selfing and sibbing in the female line into account. The adjusted percentage of hybridity corrects for these factors by subtracting non-hybrid seed produced from female plants. The ASOCA publication of hybrid alfalfa certification provides the correction factor for non-hybrid seed produced from female plants from sibbing and selfing. The correction factor is equal to P.P.I.×0.595, with the P.P.I. (Pollen production index) defined as follows.

1. Male Sterile Plants (MS) P.P.I.=0
   No visible pollen can be observed with the naked eye when flower is tripped with a black knife blade.
2. Partial Male Sterile Plants (PMS) P.P.I.=0.1
   A trace of pollen can be observed with the naked eye when flower is tripped with a black knife blade.
3. Partial Fertile Plant (PF) P.P.I.=0.6
   Less than normal amount of pollen can be observed with the naked eye when flower is tripped with a black knife blade.
4. Fertile Plant (F) P.P.I.=1.0
   Normal amounts of pollen can be observed when flower is tripped with a black knife blade.

In this example embodiment of the invention, the pollen production index (P.P.I.) is determined by sampling 200 female plants from the female rows of the "check" plots. The percentage of hybridity can then be determined by the equation:

$$\% \text{ hybridity} = \% \text{ female seed} - \% \text{ non-hybrid female seed},$$

where the % non-hybrid female seed is P.P.I.×0.595

In one preferred embodiment of the invention, the methods for producing a hybrid seed product determines the percentage of hybridity for each female to male ratio of 1:1, 2:1, 3:1, and 4:1.

This method for determining the percentage of hybridity requires analysis of seed produced by female plants apart from analysis of seed produced by pollenizer plants. Harvesting female plants separately from pollenizer plants is one way of obtaining female seed apart from pollenizer seed. However, separate harvesting of female plants from pollenizer plants is difficult under current hybrid seed production methods.

In one method for hybrid seed production, female plants are crossed with pollenizer plants by planting female plants and pollenizer plants in separate rows of plants, with each row separated by a width of twenty to forty inches. Each group of rows contain either pollenizer plants or female plants, such as shown in U.S. Pat. No. 4,045,912, herein incorporated by reference. This allows female plants and pollenizer plants to be harvested separately according to rows. However, this method involves a large physical separation of female and pollenizer plants, resulting in lower production of hybrid seed.

Female and pollenizer plants may also be intermingled in the same row in the same test plot. This intermingling increases hybrid seed production from the female plants. However, intermingling also causes difficulty in distinguishing the female plants from the pollenizer plants. To obtain data on hybrid seed production, seed from female plants must be distinguished from seed from pollenizer plants. Distinguishing between female plants and pollenizer plants is a highly labor intensive, difficult and expensive process. U.S. Pat. No. 4,045,912 provides one example of such a process, where female and pollenizer plants are germinated separately, and then hand planted and tagged in a test plot. This process becomes untenable in larger applications. Thus, the present invention provides methods for distinguishing female plants from pollenizer plants suitable for large-scale applications, such as large test plots.

The preferred embodiment of the invention for producing a hybrid seed product provides for methods for distinguishing female plants from pollenizer plants by planting female lines and pollenizer lines in subrows. The subrow methods of the invention further allow for separate harvesting of female plants and pollenizer plants. During planting, female plants and pollenizer plants are offset from the center of a row on opposite sides to distinguish the female plants from the pollenizer plants.

Figure 3:
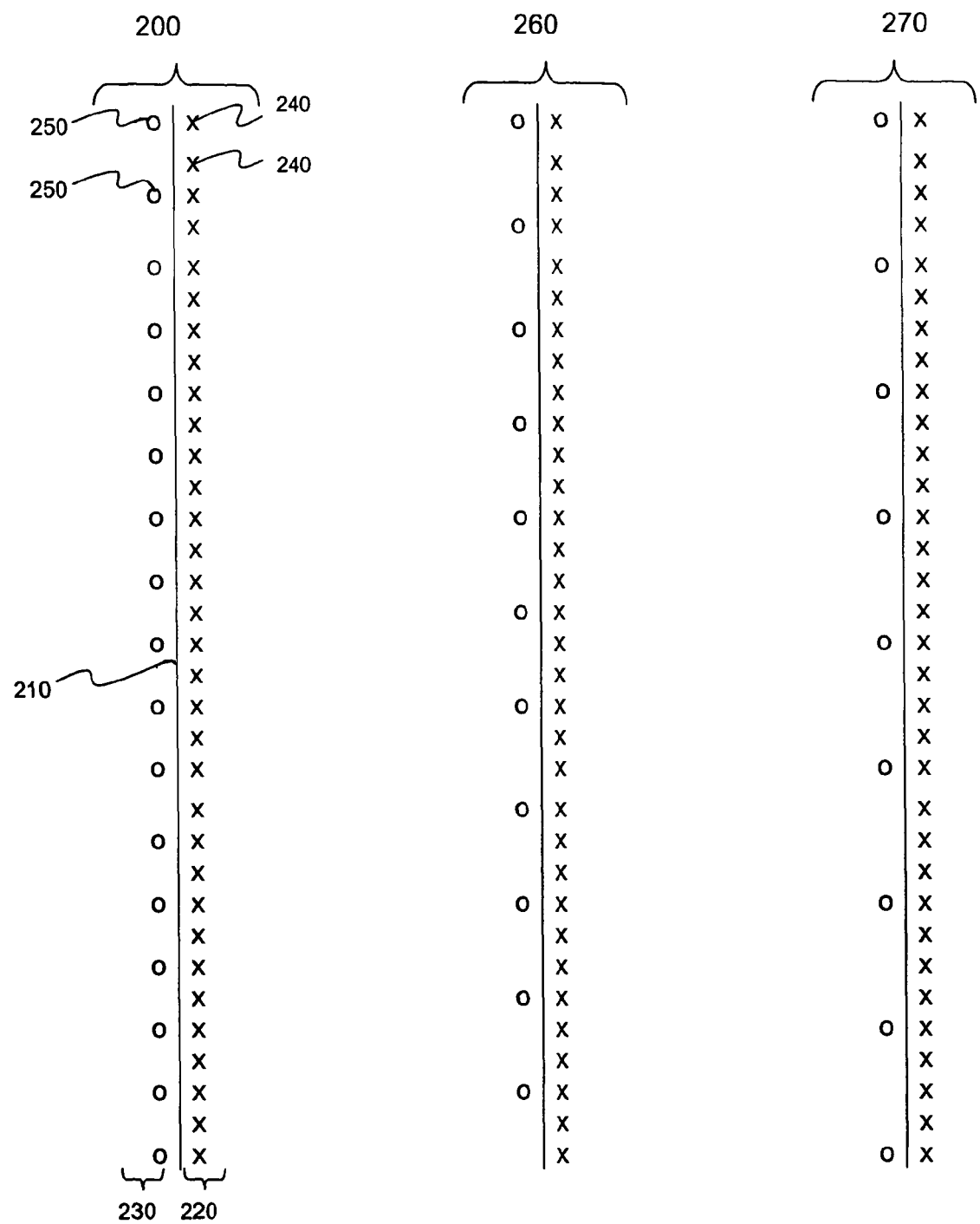
FIG. 3 shows a plot planted according to the subrow method of the invention.

FIG. 3 shows an example embodiment of the subrow planting method of the invention. The subrow planting method provides for planting both female and pollenizer plants in a single row 200, with female seed planted two to four inches from the center 210 of the row 200 on a first subrow 220, and pollenizer seed are planted one to eight inches from the center 210 of the row 200 in a second subrow 230 on the opposite side. Thus, in this example embodiment, planting according to the subrow methods provides female plants 240 offset to one side in the first subrow 220 and a pollenizer plants 250 in the second subrow 220 offset to the other side. This single row 200 shows an embodiment having a female to pollenizer ratio of 2:1. A second single row 260 shows an embodiment having a female to pollenizer ratio of 3:1. A third single row 270 shows a female to pollenizer ratio of 4:1. In one preferred embodiment of the invention, an onion planter may be used to plant female seed and pollenizer seed in their respective subrows. Those skilled in the art will recognize that other methods of planting the female seed and the pollenizer seed in their respective subrows lies within the spirit and scope of the invention.

In other aspects of the subrow methods of the invention, the subrows 220, 230 can advantageously provide for reduction of competition between female plants and male plants by increasing physical separation of the female plants from the pollenizer plants while still allowing intermingling. In cases where one line may be more vigorous than another, the increased separation between plants may allow slower growing plants a better opportunity to grow without being crowded out by other plants. Because of the small seed size of some field crops, such as alfalfa, during planting, some seeds are not spaced with sufficient room to grow, allowing a faster growing plant to crowd out a slower developing plant, particularly in subsequent years of perennial crops. Subrows provide for increased separation between female plants and pollenizer plants that reduces competition between the female plants and pollenizer plants, maintaining a more consistent female to pollenizer ratio. As the female to pollenizer ratio is selected to optimize production of the hybrid seed product, in this aspect of the present invention, planting in subrows in the production field maintains optimal production from year to year.

In another aspect of the subrow methods of the invention, subrows 220, 230 allow a breeder to quickly determine the actual female to pollenizer ratio. At a seedling stage, the subrows 220, 230 allow the number of female plants 240 and the number of pollenizer plants 250 to be quickly counted. In subsequent years after planting for perennial plants, a new female to pollenizer ratio needs to be determined from year to year, as plants may die over the winter. In this instance, subrows 220, 230 facilitate quick determination of female to pollenizer ratio through visual inspection.

In another aspect of the invention, subrows 220, 230 facilitate separate harvesting of female plants 240 and pollenizer 250 by harvesting according to female subrows and pollenizer subrows. Separate harvesting allows for determination of percentage of hybridity by sampling before harvest.

In an alternate embodiment of the invention, morphological markers, such as seed size, seed color, seed weight, leaf shape, leaf size, root color, stem color, flower color root structure, plant height and fall growth habit flower colors, can be used to distinguish female plants from pollenizer plants in the test plots. Those skilled in the art will recognize that other methods of distinguishing female plants from pollenizer plants can be employed without departing from the spirit and scope of the invention.

The preferred form of the invention further includes verification of percentage of hybridity of the hybrid seed product 140. These methods involve progeny testing and are employed after production of the hybrid seed product in the production field. Verification of percentage of hybridity can be used to help ensure a hybrid seed product achieves predetermined hybridity goals. In the preferred embodiment, a characteristic of the hybrid seed that has a distinct difference from non-hybrid seed is used in the verification process. However, as those skilled in the art will understand, other methods for verifying percentage of hybridity can be employed without departing from the spirit or scope of the invention.

In one preferred form, verifying percentage of hybridity begins with choosing a row and sampling 200-1000 female plants and 200-1000 pollenizer plants. Data is collected to determine the seed yield of the female plants and the seed yield of the pollenizer plants. The female to pollenizer ratio is determined by counting number of female plants to number of pollenizer plants for 200 feet in a chosen row for two to five replications in a hybrid seed production field. The subrow system can be employed to aid tracking of female plants versus the pollenizer plants to distinguish the plants in the commercial hybrid seed production field.

Analysis on the gathered data then provides an estimated percentage of hybridity. Because of the variability inherent in biological systems, the analysis provides an estimate rather than an exact determination. The analysis can be performed according to the following procedures:

1. From the sampled plants, determine the average female seed yield (X) to pollenizer seed yield (Y) per plant and determine average number of seed produced from female (hybrid) plants to number of seed produced from pollenizer plants as X:Y.

2. Determine number of female plants to number of pollenizer plants in a commercial hybrid seed production field by measuring the number of female plants and number of pollenizer plants in 100 feet of a randomly selected row with two to five replications. The proportion of female plants to the number of pollenizer plants is A:B.

3. The percentage of hybridity is computed according to:

$$\% \text{ Hybridity} = \frac{(A \times X)}{(A \times X) + (B \times Y)} \times 100\% - CF$$

where CF is a correction factor to account for non-hybrid seed produced from female plants by selfing, and is equal to the P.P.I. (female plants)×0.595.

Harvesting the center two rows of pollenizer line from the pollenizer test strip and harvesting the center two rows of the female line from the female test strip separately provides for data on seed size distribution of the pollenizer seed and hybrid seed. The commercial hybrid production field is harvested in bulk.

In another example embodiment, seed size distribution differential between hybrid seed and pollenizer seed provides data for verifying percentage of hybridity. In this method, four to six rows of 200-1000 feet of plants from a selected pollenizer line are planted as a pollenizer test strip and four to six rows of 200-1000 feet of plants from a selected female line are planted as a female test strip in the same commercial hybrid seed production field.

Analysis of the pollenizer seed provides the pollenizer seed size distribution. Likewise, analysis of the female seed provides the female seed size distribution, and analysis of the bulk-harvested seed provides the seed size distribution of the commercial hybrid production field. By way of illustration and not limitation, the following shows an example with the seed size distribution determined for each increment from $\frac{1}{10}$ inch to $\frac{1}{25}$ inch. In this example, samples having the same weight are used to determine the seed size distributions. The following procedure provides an estimate of the percentage of hybridity.

1. Perform a T-test for seed size distribution of pollenizer seed, hybrid seed and commercial experimental hybrid seed (female:pollenizer ratio block used by commercial hybrid seed production field) harvested from a test plot, and comparing with pollenizer seed, hybrid seed and commercial hybrid seed harvested from a commercial hybrid seed production field.

2. If the T-test is not significant, then the percentage of hybrid seed in the overlap area of the seed size distribution in the test plot would be same as overlap area of the seed size distribution in the commercial hybrid production seed field.

The % hybridity in the commercial hybrid production seed field can then be determined by:

$$\% \text{ Hybridity} = \frac{X1 + Y2}{X1 + Y2 + Q2 + R1} \times 100\% - CF$$

Where:
X=Hybrid seed weight of non-overlap area.
X1=X/1,000 seed weight of non-overlap area.
Y=Hybrid seed weight and pollenizer seed weight of overlap area.
Y1=Y×% Hybrid seed overlap area (from test plots).
Y2=Y1/1,000 seed weight.
Q=Pollenizer seed weight of overlap area.
Q1=Y×% Pollenizer seed of overlap area.
Q2=Q/1,000 seed weight.
R=Pollenizer seed weight of non-overlap area.
R1=R/1,000 seed weight.
CF=P.P.I. (female plants) X 0.595.

In an alternate embodiment, seed size distribution can be used to verify percentage of hybridity using the proportion of seed within a selected seed size range. The selected seed size range includes an area of overlap in the seed size distribution between the seed size distribution of the female seed and pollenizer seed. The percentage of hybridity can be estimated as:

$$\% \text{ Hybridity} = \frac{Z - Y}{X - Y} \times 100\% - CF$$

where:
X=percentage of female seed falling into the selected seed size range;
Y=percentage of pollenizer seed falling into the selected seed size range;
Z=percentage of production seed falling into the selected seed size range; and
CF=correction factor to account for non-hybrid seed produced from female plants by selfing, and is equal to the P.P.I. (female plants)×0.595.

As those skilled in the art will recognize, other seed characteristics where the female seed has a distinct difference from the pollenizer seed can be used to estimate the percentage of hybridity. For example, in an alternate embodiment, the mean seed size of the seed sampled from the pollenizer plants, the female plants and the production field can be used to estimate percentage of hybridity. Using this method, percentage of hybridity can be estimated as:

$$\% \text{ Hybridity} = \frac{Z - Y}{X - Y} \times 100\% - CF$$

where:
X=mean female seed size;
Y=mean pollenizer seed size;
Z=mean production seed size; and CF=correction factor to account for non-hybrid seed produced from female plants by selfing and sibbing, equal to the P.P.I. (female plants)×0.595.

In another example embodiment, the methods for verification of percentage of hybridity employ the pollen production index (P.P.I.) of hybrid seed and the commercial hybrid seed product, which is a mixture of hybrid and pollenizer seed. In this embodiment of the invention employing the P.P.I., verification of percentage of hybridity begins with crossing a selected female line with a selected pollenizer line and harvesting the seed produced by the cross in a test plot and production field. The harvested seed is planted and P.P.I. data is gathered. Further analysis for verification of hybridity proceeds in one of two cases, depending on whether the P.P.I. of the hybrid seed production field is larger than the P.P.I. of the test plot hybrid seed or vice versa.

Case 1

If the P.P.I. of the hybrid seed production field is larger than the P.P.I. of the test plot hybrid seed, the following formula will be used to calculate the percentage of hybridity.

The seed from a hybrid seed production field contain both hybrid seed (female×pollenizer) and non-hybrid seed (pollenizer). The seed from test plot of f:p=1:0 contains only hybrid seed.

% of hybridity=1-P.P.I. (Production seed)/1-P.P.I. (Test plot hybrid seed)×100-CF      a Sample size of growouts=200-2000 plants from each population (production seed and test plot hybrid seed) at the same environment and same location.      b Case 2

If the P.P.I. from the hybrid seed production field is similar to the P.P.I. of the test plot hybrid seed, then seed size distribution differential between hybrid seed and pollenizer seed or some morphological traits or molecular markers that can differentiate hybrid seed from non-hybrid seed from grow outs need to be used to verify the percentage of hybridity.

As the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

I claim:

1. A method for producing a hybrid seed product of a bee-pollinated crop, from a cross between female plants from at least one female line and pollenizer plants from at least one pollenizer line, the hybrid seed product having a percentage of hybridity above a predetermined percentage of hybridity, the method comprising:

(a) selecting the at least one female line and the at least one pollenizer line to have a seed size differential between seed of the female plants and seed of the pollenizer plants;

(b) planting the at least one female line and the at least one pollenizer line in a production ratio in a production field such that the at least one female line and the at least one pollenizer lines are crossed to obtain the total seed product comprising hybrid seed and non-hybrid seed, wherein the hybrid seed and non-hybrid seed in the production seed each have a seed size distribution and the seed size distributions overlap by less than twenty-five percent of the production seed; and (c) removing at least a portion of the non-hybrid seed from the hybrid seed to achieve a post-production increase of percentage of hybridity and obtain the hybrid seed product having a percentage of hybridity above the predetermined percentage of hybridity.

2. The method of claim 1 wherein the bee-pollinated crop is alfalfa.

3. The method of claim 1 wherein the bee-pollinated crop is soybean.

4. The method of claim 1 wherein the predetermined percentage of hybridity comprises seventy-five percent.

5. The method of claim 1 wherein the production ratio of step (b) is determined by selecting a ratio of the female line to the pollenizer line to maximize yield of the total seed product in the production field or yield of the hybrid seed product in the production field, while maintaining the percentage of hybridity of the hybrid seed product above the predetermined percentage of hybridity.

6. The method of claim 1 wherein selecting the at least one female line and the at least one pollenizer line in step (a) comprises:
selecting the at least one female line and the at least one pollenizer line to provide a cross maintaining at least two-thirds of female seed yield when increasing ratio of female plants to pollenizer plants from 1:1 to 3:1 under substantially similar environmental conditions.

7. The method of claim 1 wherein selecting the at least one female line and the at least one pollenizer line comprises selecting a female line having an average Pollen Production Index (P.P.I.) between 0.0% to 0.42%.

8. The method of claim 1 wherein selecting the at least one female line and the at least one pollenizer line comprises selecting a pollenizer line having high self-incompatibility.

9. The method of claim 1 further comprising crossing the female plants with the pollenizer plants at a test ratio of female plants to pollenizer plants in a test plot to obtain a test seed product having a test percentage of hybridity, wherein the production ratio of female plants to pollenizer plants needed to produce the hybrid seed product having a percentage of hybridity above seventy-five percent is estimated from the test percentage of hybridity.

10. The method of claim 9 wherein the test percentage of hybridity is determined by harvesting the test seed product; and determining the proportion of hybrid seed in the test seed product.

11. The method of claim 10 wherein crossing the female plants with the pollenizer plants at the test ratio in the test plot further comprises planting female plants and pollenizer plants in the test plot, the test plot having multiple rows, with the female plants planted in a female subrow offset from the centerline of each row of the multiple rows on a first side, and the pollenizer plants planted in a pollenizer subrow offset from the centerline of each row on an opposite side.

12. The method of claim 1 wherein substantially all the non-hybrid seed is removed in step (c) by screening through a sieve.

13. The method of claim 1 further comprising crossing the female plants and the pollenizer plants at multiple test ratios of female plants to pollenizer plants to determine a respective test percentage of hybridity for each of the multiple test ratios.

14. The method of claim 13 wherein the production ratio of step (b) is determined by: performing a regression analysis on the multiple test ratios test percentage and the respective test percentage of hybridity; and using the regression analysis to determine the production ratio of female plants to pollenizer plants to produce the hybrid seed product having a percentage of hybridity above seventy-five percent.

15. The method of claim 1 further comprising verifying the percentage of hybridity of the hybrid seed product by progeny testing.

16. The method of claim 15 further comprising using molecular markers to identify the hybrid seed and the non-hybrid seed to determine percentage of hybridity of the hybrid seed product.

17. The method of claim 15 wherein verifying percentage of hybridity for the hybrid seed product further comprises:
collecting female seed data on traits of the female seed;
collecting pollenizer seed data on traits of the pollenizer seed;
collecting hybrid seed product data on traits of the hybrid seed product; and
analyzing the female seed data, the pollenizer seed data and the hybrid seed product data to estimate a percentage of hybridity for the hybrid seed product.

18. The method of claim 1 further comprising killing the pollenizer plants prior to harvest to increase the percentage of hybridity of the production seed.

19. The method of claim 1, wherein selecting the at least one female line and the at least one pollenizer line to have a seed size differential further comprises selecting the female line to have a seed size larger than the pollenizer line seed size.

20. The method of claim 1, wherein the portion of non-hybrid seed is removed from the non-hybrid seed by sieving through a sieve size from 1/19 inches to 1/23 inches.

21. The method of claim 1, wherein the hybrid seed product is produced at commercial levels of production.

* * * * *